United States Patent
Kuipers

(10) Patent No.: US 9,150,412 B2
(45) Date of Patent: Oct. 6, 2015

(54) METHOD FOR PRODUCING A FUNCTIONAL UNIT AND CORRESPONDING FUNCTIONAL UNIT

(71) Applicant: KROHNE Messtechnik GmbH, Duisburg (DE)

(72) Inventor: Winfred Kuipers, Essen (DE)

(73) Assignee: KROHNE Messtechnik GmbH, Duisburg (DE)

(*) Notice: Subject to any disclaimer, the term of this patent is extended or adjusted under 35 U.S.C. 154(b) by 0 days.

(21) Appl. No.: 14/449,317

(22) Filed: Aug. 1, 2014

(65) Prior Publication Data
US 2015/0037210 A1 Feb. 5, 2015

(30) Foreign Application Priority Data
Aug. 1, 2013 (DE) .................. 10 2013 012 731

(51) Int. Cl.
| | | |
|---|---|---|
| B81C 3/00 | (2006.01) | |
| B81B 7/02 | (2006.01) | |
| B81C 1/00 | (2006.01) | |
| G01N 27/62 | (2006.01) | |
| G01N 30/68 | (2006.01) | |
| G01N 30/60 | (2006.01) | |
| G01N 30/88 | (2006.01) | |

(52) U.S. Cl.
CPC . *B81C 3/001* (2013.01); *B81B 7/02* (2013.01); *B81C 1/00341* (2013.01); *G01N 27/626* (2013.01); *G01N 30/68* (2013.01); *B81B 2201/0292* (2013.01); *B81C 2201/019* (2013.01); *G01N 30/6095* (2013.01); *G01N 2030/8881* (2013.01)

(58) Field of Classification Search
CPC ... G01N 30/68; G01N 27/262; B81C 1/00341
USPC .......................................................... 422/54
See application file for complete search history.

(56) References Cited

U.S. PATENT DOCUMENTS

| | | | |
|---|---|---|---|
| 3,762,878 A | | 10/1973 | Villalobos |
| 4,109,377 A | * | 8/1978 | Blazick et al. .................. 29/831 |
| 5,292,479 A | | 3/1994 | Haraga et al. |
| 6,527,890 B1 | * | 3/2003 | Briscoe et al. ............. 156/89.11 |
| 6,572,830 B1 | | 6/2003 | Burdon et al. |
| 6,592,696 B1 | | 7/2003 | Burdon et al. |
| 6,786,716 B1 | | 9/2004 | Gardner et al. |
| 7,608,818 B2 | * | 10/2009 | Miller et al. .................. 250/288 |
| 8,305,086 B2 | | 11/2012 | Jörg et al. |

(Continued)

FOREIGN PATENT DOCUMENTS

| | | | |
|---|---|---|---|
| DE | 198 14 659 C1 | | 10/1999 |
| WO | WO 2012055835 | * | 5/2012 |

OTHER PUBLICATIONS

Wu, M H and Yetter, R.A. "Development and analysis of a LTCC micro stagnation-point flow combustor." (2008). J. Micromech. Microeng. 18.*

*Primary Examiner* — Jill Warden
*Assistant Examiner* — Jacqueline Brazin
(74) *Attorney, Agent, or Firm* — Roberts Mlotkowski Safran & Cole, P.C.; David S. Safran

(57) ABSTRACT

A method for producing a functional unit with a gas converter (1) and a flame ionization detector (10) is produced with the gas converter (1) and the flame ionization detector (10) being connected together as parts of a multi-layer ceramic (6).

1 Claim, 4 Drawing Sheets

(56) References Cited

U.S. PATENT DOCUMENTS

| | | | |
|---|---|---|---|
| 2003/0194363 A1* | 10/2003 | Koripella et al. | 422/222 |
| 2007/0084346 A1 | 4/2007 | Boyle et al. | |
| 2007/0154367 A1* | 7/2007 | Jang et al. | 422/189 |
| 2012/0141946 A1 | 6/2012 | Müller et al. | |
| 2014/0035593 A1 | 2/2014 | Kuipers | |

* cited by examiner

METHOD FOR PRODUCING A FUNCTIONAL UNIT AND CORRESPONDING FUNCTIONAL UNIT

BACKGROUND OF THE INVENTION

1. Field of the Invention

The invention relates to a method for producing a functional unit with a gas converter and a flame ionization detector. Furthermore, the invention relates to a functional unit having a gas converter and a flame ionization detector. The gas converter is used here, in particular, at least partially for transforming a gas or a gas mixture as medium to be converted or transformed.

2. Description of Related Art

Microsystems technology is used for producing structures or components with small-scale dimensions.

In low temperature co-fired ceramics (LTCC), un-sintered—so-called green—ceramic sheets are individually structured, stacked, laminated (laminating generally meaning the joining of layers by means of adhesives) and subjected to a sinter profile at a maximum temperature between ca. 850° C. and 900° C. The LTCC method differs from the production of high temperature co-fired ceramics (HTCC) in the maximum temperatures occurring during sintering, where sintering occurs at temperatures between 1600° C. and 1800° C. Thick film hybrid technologies are also known, wherein conductor paths or resistors are applied to previously-sintered ceramic substrates using screen printing. If the printed carrier is sintered, the applied pastes melt into layers. Then, discrete components are possibly mounted.

One area of use for microsystems technology is, for example, the production of flame ionization detectors. Hydrocarbons are ionized in a hydrogen flame in flame ionization detectors (FID). The flow of ions is, then, a measure for the organic carbon content of the sample to be tested.

A description of a flame ionization detector can be found in International Patent Application Publication WO 2009/036854 A1 and corresponding U.S. Pat. No. 8,305,086 B2. The description of a counter-flow combustor in International Patent Application Publication WO 2011/015285 A2, that corresponds to U.S. Patent Application Publication 2012/0141946 A1, or a counter-flow combustor for a flame ionization detector as disclosed in International Patent Application Publication WO 2012/055835 A1 are relevant in this context.

A method for producing a flame ionization detector can be seen in commonly owned U.S. Patent Application Publication 2014/0035593 A1.

Catalytic gas converters or gas transformers—in part as a preliminary stage—are used in operating flame ionization detectors.

If normal, ambient air is used as the air for sintering, then traces of organic compounds are transformed by means of thermal catalysis in $CO_2$. This, for example, occurs in that sintering air is drawn in from the surroundings via a catalyzer.

Since methane is further present in the air in relatively high concentrations as a trace gas (in part up to 1800 ppb as opposed to 1 ppb for other hydrocarbons), a difference is made between the entire hydrocarbon content and the methane hydrocarbon content. In order to determine the methane hydrocarbon content, the remaining organic compounds are initially removed by means of catalytic oxidation.

Furthermore, carbon monoxide CO and carbon dioxide $CO_2$ can be quantified by means of catalytic methanation, even though flame ionization detectors are principally not sensitive to these compounds. The catalytic methanation, thereby occurs by adding hydrogen at a temperature between 350 and 370° C. following this sequence:

$$CO+3H_2 \rightarrow CH_4+H_2O \text{ and } CO_2+4H_2 \rightarrow CH_4+2H_2O.$$

This, thus, demonstrates the great advantage of the use of gas converters in conjunction with flame ionization detectors.

Miniaturized converters for transforming liquid methanol into hydrogen for fuel cells, which consist of multi-layer ceramics, can, for example, be seen in the application publications U.S. Patent Application Publication 2007/0154367 A1 or WO 03/088390 A2 corresponds to U.S. Patent Application Publication 2003/0194363 A1.

Different materials for catalyzers for air treatment are disclosed, for example, in German Patent Application DE 691 17 048 A1 and corresponding U.S. Pat. No. 5,292,479.

Catalyzers for producing nanotubes for a gas chromatograph are disclosed, for example, in U.S. Patent Application Publication 2007/0084346 A1.

A difficulty in the use of flame ionization detectors and gas converters, which are characterized overall by their interaction as functional unit, lies in the type of arrangement and connection of components. For example, a safe transmission for the gas converted by the gas converter to the detector must be implemented. Accordingly, this increases the demands on the connections of the detector or converter. Furthermore, sufficient safety must be ensured when dangerous media are used.

SUMMARY OF THE INVENTION

A primary object of the invention is to provide a method for producing a functional unit with a gas converter and a flame ionization detector that is an improvement over the prior art.

The method according to the invention, in which the above derived and described object is achieved, is initially and essentially wherein the gas converter and the flame ionization detector are produced together of a multi-layer ceramic.

The gas converter produced as a part of the functional unit is used for the, at least partial, transformation of a gas or gas mixture, of which at least one component is to be at least partially converted—in particular, assisted by at least one catalyzer layer. The gas converter according to the invention is, thus, a micro gas converter, which is implemented in a multi-layer ceramic, which is formed of several ceramic layers joined into one unit. In that, the gas converter and the flame ionization detector are produced together in the multi-layer ceramic that they result in a very compact functional unit. A great advantage is that interfaces within the multi-layer ceramic can be produced in this manner.

Thereby, the gas converter is, in particular, functionally and possibly also spatially upstream to the flame ionization detector.

Microsystems technology is used as a method for producing the gas converter and the flame ionization detector.

In one design, it is provided, in particular, that lost heat from the flame ionization detector is used for the catalytic processes of the gas converter. In this manner, for example, heat from the flame ionization detector is conveyed through the gas converter by corresponding structures.

Alternatively or additionally, at least one heating structure is provided on or in a layer of the multi-layer ceramic as part of the gas converter in order to control or cause the conversion by means of catalysis. Such a heating structure is, for example, tapped with an electric current and warms the medium or catalyzer layer to be converted.

In one design, the production of the functional unit occurs in that at least one medium outlet of the gas converter is connected to the flame ionization detector.

Medium channels—e.g., in the form of recesses, holes or boreholes—are provided in one design in the gas converter or layers of the multi-layer ceramic. This aids in the implementation of the functional unit as monolithic multi-layer ceramic and in the transmission of the gas or gas mixture to be converted or in allowing involved substances within the multi-layer ceramic.

The above medium outlet of the gas converter is thus simultaneously a medium channel within the multi-layer ceramic—in particular, in conjunction with a medium inlet of the flame ionization detector.

In one design, in particular, several gas converters—either identical or different—are arranged in a multi-layer ceramic.

In particular, in one design, at least one catalyzer layer is applied to a layer of the multi-layer ceramic in the production of the gas converter.

It is provided in one design that at least one medium-guiding channel—in particular in the form of a recess—is produced in at least one layer of the multi-layer ceramic for the gas converter. The guided medium is, thereby, in particular, a gas or a gas mixture.

In one design, in conjunction with a medium-guiding channel, it is provided that the catalyzer layer and the medium-guiding channel are produced in such a manner that the medium-guiding channel guides a medium at least partially past the catalyzer layer. A chemical transformation occurs due to contact with the catalyzer layer. In one variation, the medium-guiding channel is, in particular, a recess in one layer of the multi-layer ceramic.

In a further design, the catalyzer layer is produced in such a manner—in particular porous in the sense of being pervious for a gaseous medium—that the catalyzer layer can at least partially have medium flowing through it—in particular, the gaseous medium to be converted or transformed. In this design, the medium doesn't flow through a medium-guiding channel over the catalyzer layer, but flows through the layer itself. The ceramic layer is, in turn, located in a medium-guiding channel. For this, the catalyzer layer is, for example, introduced on a layer of the multi-layer ceramic with a thick film method.

For practical implementation, it is provided in one design that at least the gas converter and the flame ionization detector are produced at least partially by means of Low Temperature Cofired Ceramic (LTCC) or High Temperature Cofired Ceramic (HTCC) technology. Thus, the structures or elements of the gas convertor or flame ionization detector are produced partially on the green ceramic layers of the multi-layer ceramic or recesses are made and these layers are sintered by the subsequent respective associated process of the technologies used.

The invention further relates to a functional unit having at least one gas converter and at least one flame ionization detector, which have been produced using one of the above-mentioned implementations of the method according to the invention. In this manner, in particular, the gas converter and the flame ionization detector are produced together in a multi-layer ceramic. Or, in other words: the functional unit is formed of at least the gas converter and the flame ionization detector and is formed overall by the multi-layer ceramic.

In one design, at least one medium outlet of the gas converter is connected to the flame ionization detector. Preferably, the connection is such that a gas or gas mixture converted by the gas converter is supplied to the flame ionization detector.

Conversely, it is provided in an alternative or additional implementation that lost heat from the flame ionization detector is used for catalytic processes of the gas converter. In this implementation, the heat from the flame ionization detector is thus conveyed to the gas converter.

In detail, there are numerous possibilities for designing and further developing the method according to the invention and the functional unit according to the invention as will be apparent from the following description of embodiments in conjunction with the accompanying drawings.

DETAILED DESCRIPTION OF THE INVENTION

Figure 1:
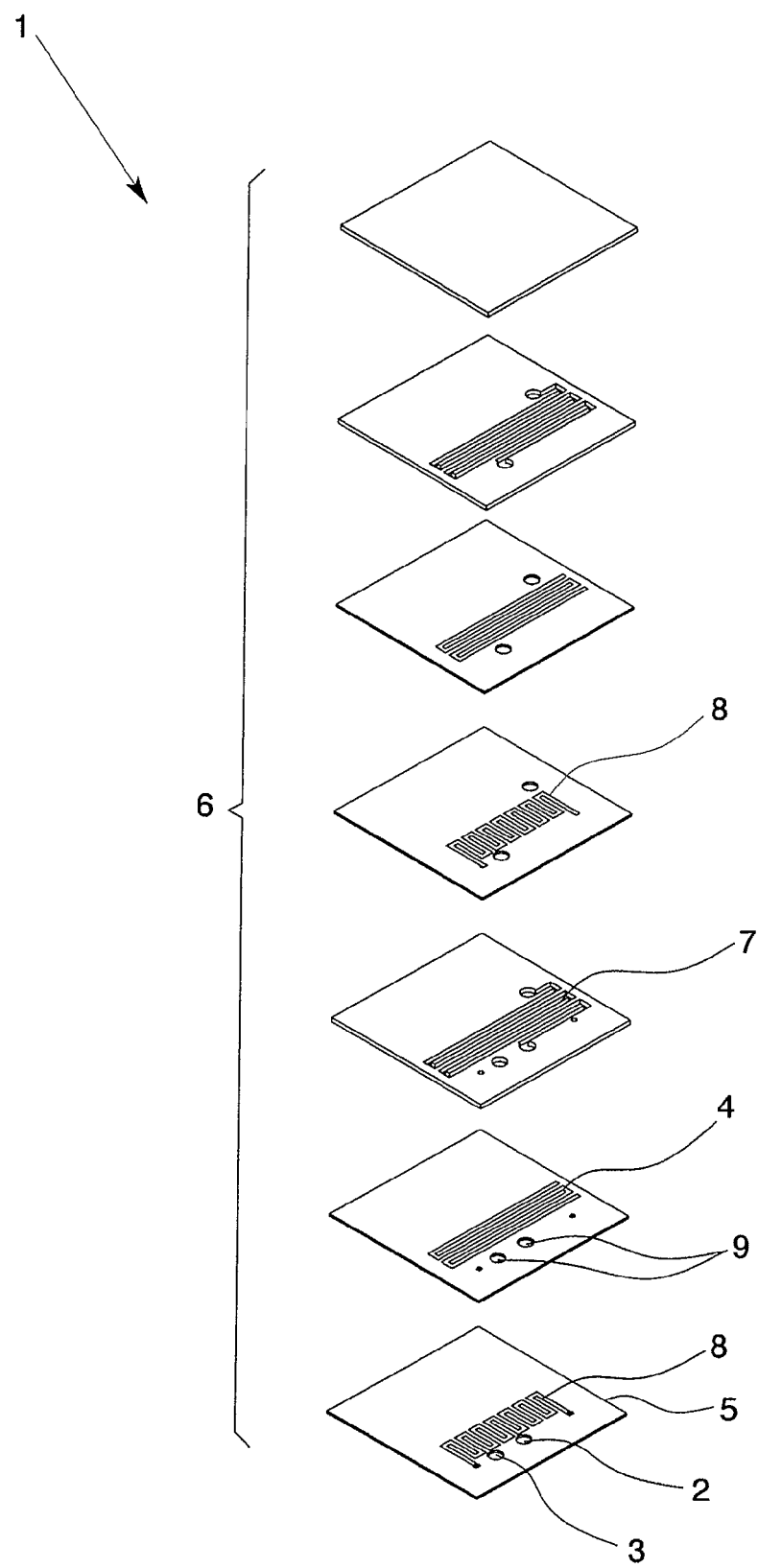
FIG. 1 is a schematic exploded view of a first embodiment of a gas converter.

FIG. 1 shows an exploded view of a gas converter 1, purely as an example and significantly reduced for clarity of the representation. A medium inlet 2 and a medium outlet 3 are located on the lowest layer, wherein the medium, in particular, is gaseous. The arrangement of the inlet 2 and outlet 3 on one side of the gas converter 1 simplifies the mounting of the gas converter 1, which can optionally be used as a surface-mounted device SMD component as a result.

Catalyzer layers 4 are provided for the conversion or transformation of the gas as medium, along which the gas flows and through which the gas or gas mixture or at least a component thereof is at last partially transformed. The catalyzer layer 4 is located on one of the many layers 5 of the multi-layer ceramic 6 that forms the micro gas converter 1.

In the illustrated embodiment, the gaseous medium flows through the medium-guiding channels 7, and thus, over the catalyzer layers 4. The medium-guiding channels 7 are thereby, in particular, designed recesses in each of the ceramic layers 5.

Heating structures 8 are located on other layers 5, which heat the medium and thus support the transformation.

The electric leads of the heating structures 8 are not shown, which partially pass through the layers 5 or have been applied to the layers 5 as electrically conductive layers. The leads are preferably led along the bottom side for SMD mounting, like the fluid feeds. Such fluid feeds relate here, in general, to the supply and lead-away of fluids, i.e., flowable or, e.g., partially liquid or gaseous media.

For movement of the medium between the layers 5, medium channels 9 are provided in the layers 5, which are designed as boreholes in the illustrated example.

Located on the layers 5 of the gas converter 1 shown in FIG. 1—illustrated from bottom to top—are a heating element 8, a catalyzer layer 4 and above it a medium-guiding channel 7, a further heating element 8 and above it a further catalyzer layer 4, on which a layer 5 with a medium-guiding channel 7 borders. The topmost layer is thereby designed as a cover. Furthermore, two boreholes are provided as medium channels 9 and are located in each of the layers—except the layer that represents the cover: one channel 9 is for the rising gas that is to be converted and one channel 9 for the gas that has already been transformed, which is conveyed to the medium outlet 3.

For example, ambient air is treated using the shown construction. Alternatively,—depending on the type of catalyzer layer—carbon monoxide and carbon dioxide can be transformed for subsequent quantification. The same holds true for methane in ambient air.

How the gas is guided in the gas converter 1 and how further substances or media are supplied or led away, can be achieved using the structure of the layers 5, wherein control elements can be provided in part, which, e.g., open or close channels for the media.

Figure 2:
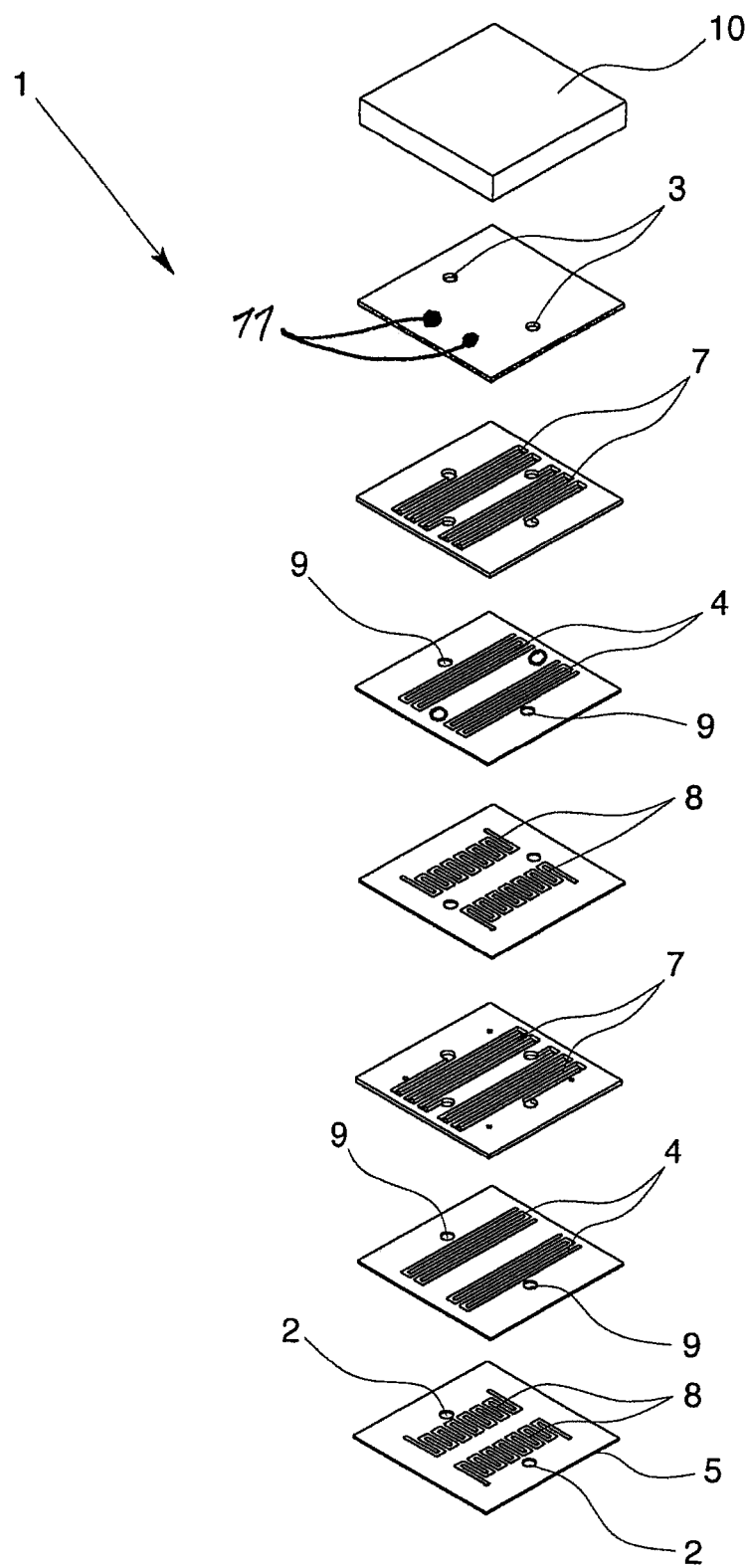
FIG. 2 is a schematic partially exploded view of a functional unit having a second embodiments of a gas converter and having a flame ionization detector.

FIG. 2 shows an embodiment, in which the gas converter 1 is directly connected to a flame ionization converter 10 and, together with it, forms a multi-layer ceramic 6 as a functional unit. The flame ionization detector 10 is, in particular, produced according to commonly owned U.S. patent application disclosed in US Patent Application Publication 2014/0035593 A1, which is hereby explicitly incorporated by reference into the present patent application.

Two medium outlets 3—for the converted gas—lead directly to the flame ionization detector 10 for the connection between the two functional units gas converter 1 and flame ionization detector 10. The structures and functional elements of the gas converter 1 are additionally designed twice on each layer 5 and oppose one another extensively in a mirror image. Different media can also be introduced due to the two medium inlets 2: e.g., the medium to be converted and a gas that is required for a special transformation—e.g., using the counter-flow method. Furthermore, a valve is optionally provided in front of the medium inlets 2, so that the medium can flow in differing quantities in the opposite direction of the gas converter 1.

A very compact configuration can be achieved for the resulting functional unit due to the direct connection between gas converter 1 and flame ionization detector 10. A further advantage results from the guiding of the waste heat from the flame ionization detector 10 through the gas converter 1, so that the waste heat is used for heating the gas to be converted.

Guiding occurs, for example, using additional boreholes in the layers 5. If a borehole is filled with a good thermal conductor—for example, a metal—a so-called "thermal via" 11 is created.

Figure 3:
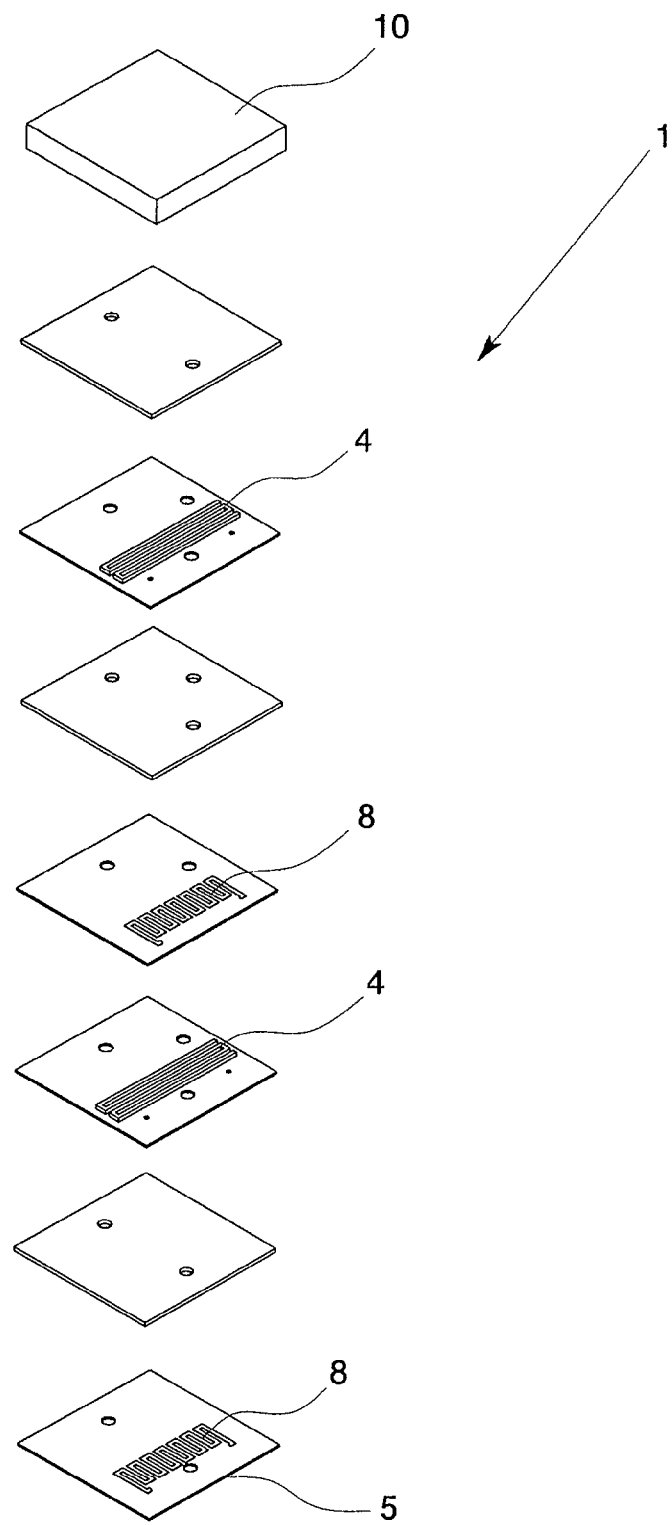
FIG. 3 is a schematic partially exploded view of a functional unit having a third embodiment of a gas converter and a flame ionization detector and FIGS. 4a & 4b show two layers of a gas converter in a top view and in a cross-sectional view, respectively.

In the embodiment of the gas converter 1 of FIG. 3, the medium flows directly through the catalyzer layers 4, which are designed thicker and porous here and which are inserted in the medium-guiding channels—not shown here.

Figure 4:
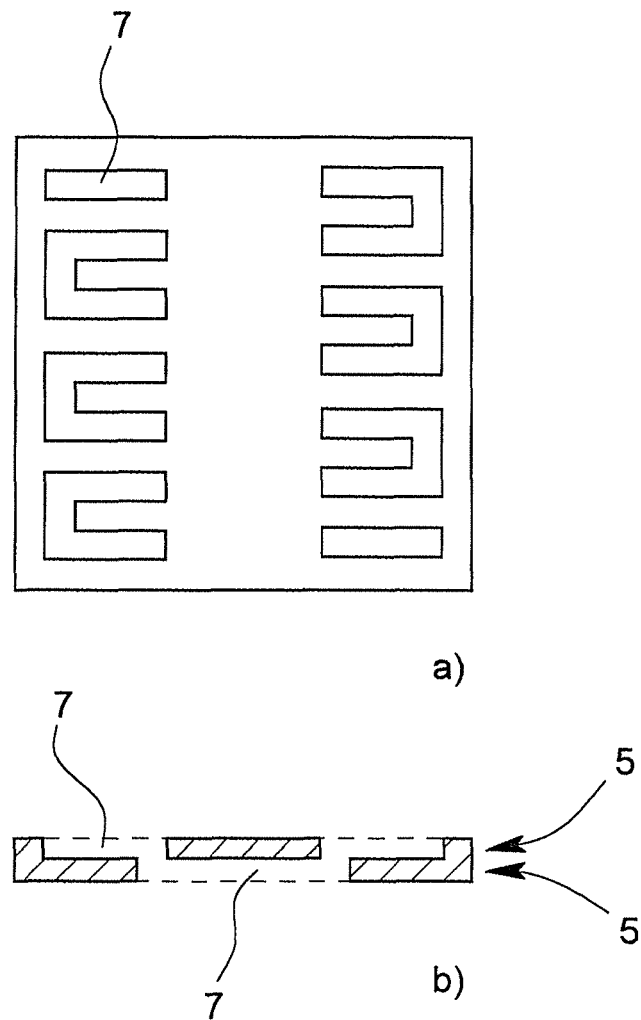

FIG. 4 shows a) a top view and b) a cross section of an embodiment of a particularly advantageously designed medium-guiding channel 7 including two layers.

Thereby, the medium-guiding channel 7 is formed in total by two layers 5, in which the recesses that complement the channels 7 are accordingly inserted. This occurs, preferably, in the green—i.e., still un-sintered—ceramic layers that are subsequently sintered. This embodiment is characterized by its increased stability.

In order to increase stability, a medium-guiding channel 7 can also—alternatively or additionally—be produced by embossing in an un-sintered ceramic layer 5, which is optionally present as a film.

What is claimed is:

1. Functional unit comprising:
   a gas converter having at least one catalyzer layer for converting at least one component of a gas mixture, and
   a flame ionization detector for measuring organic carbon content of the gas mixture with the converted component,
   wherein the gas converter and the flame ionization detector being directly connected parts of a multi-layer ceramic formed of ceramic layers sintered together,
   wherein the gas converter is followed by the flame ionization detector,
   wherein at least one medium outlet of the gas converter for the gas mixture with the converted component is connected to the flame ionization detector, and
   wherein a waste heat outlet of the flame ionization detector is connected to the gas converter a thermal via enabling use of waste heat for heating the gas mixture.

\* \* \* \* \*